United States Patent
Riggs-Sauthier et al.

(10) Patent No.: US 10,463,744 B2
(45) Date of Patent: Nov. 5, 2019

(54) POLYMER-SEMAXANIB MOIETY CONJUGATES

(71) Applicant: Nektar Therapeutics, San Francisco, CA (US)

(72) Inventors: Jennifer Riggs-Sauthier, Huntsville, AL (US); Stephanie Allums-Donald, Madison, AL (US); Sean M. Culbertson, Gurley, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 15/910,830

(22) Filed: Mar. 2, 2018

(65) Prior Publication Data

US 2018/0185496 A1 Jul. 5, 2018

Related U.S. Application Data

(62) Division of application No. 13/995,301, filed as application No. PCT/US2011/067175 on Dec. 23, 2011, now Pat. No. 9,943,605.

(60) Provisional application No. 61/426,880, filed on Dec. 23, 2010.

(51) Int. Cl.
*A61K 31/404* (2006.01)
*A61K 47/54* (2017.01)
*A61K 47/60* (2017.01)
*C07D 209/34* (2006.01)

(52) U.S. Cl.
CPC ............ *A61K 47/545* (2017.08); *A61K 47/60* (2017.08); *A61K 31/404* (2013.01); *C07D 209/34* (2013.01)

(58) Field of Classification Search
CPC .... A61K 31/404; A61K 47/545; A61K 47/60; C07D 209/34
See application file for complete search history.

(56) References Cited

U.S. PATENT DOCUMENTS

| | | | |
|---|---|---|---|
| 4,810,646 | A | 3/1989 | Jamas et al. |
| 4,992,540 | A | 2/1991 | Jamas et al. |
| 5,028,703 | A | 7/1991 | Jamas et al. |
| 5,607,677 | A | 3/1997 | Jamas et al. |
| 5,741,495 | A | 4/1998 | Jamas et al. |
| 5,932,462 | A | 8/1999 | Harris et al. |
| 6,147,106 | A | 11/2000 | Tang et al. |
| 6,610,688 | B2 | 8/2003 | Liang et al. |
| 6,906,093 | B2 | 6/2005 | Tang et al. |
| 6,908,930 | B2 | 6/2005 | Liang et al. |
| 7,026,440 | B2 | 4/2006 | Bentley et al. |
| 7,202,265 | B2 | 4/2007 | Tang et al. |
| 2005/0009988 | A1 | 1/2005 | Harris et al. |
| 2005/0079155 | A1 | 4/2005 | Marshall |
| 2005/0136031 | A1 | 6/2005 | Bentley et al. |
| 2005/0281781 | A1 | 12/2005 | Ostroff |
| 2008/0044438 | A1 | 2/2008 | Ostroff et al. |
| 2014/0011855 | A1 | 1/2014 | Riggs-Sauthier et al. |

FOREIGN PATENT DOCUMENTS

| | | |
|---|---|---|
| WO | WO 2005/058309 A1 | 6/2005 |
| WO | WO 2005/107815 | 11/2005 |
| WO | WO 2005/108463 | 11/2005 |
| WO | WO 2009/141823 | 11/2009 |
| WO | WO 2010/120387 A1 | 10/2010 |
| WO | WO 2010/120388 A1 | 10/2010 |
| WO | WO 2012/088522 | 6/2012 |
| WO | WO 2012/088529 | 6/2012 |

OTHER PUBLICATIONS

Leaf, Fortune, 2004, Time Inc., pp. 1-26 (Year: 2004).*
Kieran et. al., Pediatric Blood & Cancer, 2009, Wiley-Liss Inc., vol. 52, pp. 169-176 (Year: 2009).*
Dowlati et. al., Clin Cancer Res., 2005, American Assoc Cancer, vol. 11(21), pp. 7938-7944 (Year: 2005).*
Watanabe et. al., Clin Cancer Res., 2005, American Assoc Cancer, vol. 11, pp. 407-409 (Year: 2005).*
Thaker et. al., Expert Reviews Neurother. Dec. 2009, NIH, vol. 9(12), pp. 1-35 (Year: 2009).*
Greenwald et al., "Poly(ethylene glycol) Conjugated Drugs and Prodrugs: A Comprehensive Review", Critical Reviews in Therapeutic Drug Carrier Systems, vol. 17, No. 2, pp. 101-161, (2000).
Mendel et al., "Development of SU5416, a selective small molecule inhibitor of VEGF receptor tyrosine kinase activity, as an antiangiogenesis agent", Anti-Cancer Drug Design, vol. 15, pp. 29-41, (2000).
Pasut et al., "Protein, peptide and non-peptide drug PEGylation for therapeutic application", Expert Opin. Ther. Patents, vol. 14, No. 6, pp. 859-894, (2004).
Rygaard et al., "Heterotransplantation of a Human Malignant Tumour to "Nude" Mice", Acta. Path. Microbiol. Scand., vol. 77, pp. 758-760, (1969).
Sun et al., "Synthesis and Biological Evaluations of 3-Substituted Indolin-2-ones: A Novel Class of Tyrosine Kinase Inhibitors That Exhibit Selectivity toward Particular Receptor Tyrosine Kinases", J. Med. Chem., vol. 41, pp. 2588-2603, (1998).
Voller et al., "Enzyme-Linked Immunosorbent Assay", Am. Soc. of Microbio. Man. of Clin. Immun., 2$^{nd}$ ed., pp. 359-371, (1980).
PCT International Search Report and Written Opinion corresponding to PCT Application No. PCT/US2011/067175 dated May 15, 2012.
PCT International Preliminary Report on Patentability corresponding to PCT Application No. PCT/US2011/067175 dated Jul. 4, 2013.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).

(Continued)

*Primary Examiner* — Sarah Pihonak
(74) *Attorney, Agent, or Firm* — Jacqueline F. Mahoney

(57) ABSTRACT

The invention relates to (among other things) polymer-semaxanib moiety conjugates and related compounds. A compound of the invention, when administered by any of a number of administration routes, exhibits advantages over the semaxanib moiety in unconjugated form.

12 Claims, 3 Drawing Sheets

(56) References Cited

OTHER PUBLICATIONS

Nektar™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003—$1^{st}$, (Jan. 2003).

NOF Corporation, PEG Derivatives, Phospholipid and Drug Delivery Materials for Pharmaceuticals, 27 pages, Catalogue 2003—$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; BIOTINS, 5 pages, (Apr. 2004).

Polypure Products, PEG amines; PEG acids and amino acids; PEG thiols and disulfides; BIOTINS, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog (Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog (Jan. 2000).

Shearwater Corporation, Polyethylene Glycol and Derivatives for Biomedical Applications, 20 pages, Catalog (Jul. 2001).

\* cited by examiner

POLYMER-SEMAXANIB MOIETY CONJUGATES

CROSS REFERENCE TO RELATED APPLICATIONS

This application is a divisional application of U.S. patent application Ser. No. 13/995,301, filed Aug. 27, 2013, which is a 35 U.S.C. § 371 application of International Application No. PCT/US2011/067175, filed Dec. 23, 2011, designating the United States, which claims the benefit of priority under 35 U.S.C. § 119(e) to U.S. Provisional Patent Application No. 61/426,880, filed Dec. 23, 2010, the disclosures of which are incorporated herein by reference in their entireties.

FIELD

This invention comprises (among other things) chemically modified forms of the receptor tyrosine kinase (RTK) inhibitor, semaxanib, which forms possess certain advantages over semaxanib lacking the chemical modification. The chemically modified forms of semaxanib and related forms of semaxanib described herein relate to and/or have application(s) in (among others) the fields of drug discovery, pharmacotherapy, physiology, organic chemistry and polymer chemistry.

BACKGROUND

Protein kinases ("PKs") are enzymes that catalyze the phosphorylation of hydroxy groups on tyrosine, serine and threonine residues within proteins. Phosphorylation of these hydroxy groups is required for the growth, differentiation and proliferation of cells. Thus, virtually all aspects of the cell life cycle depend on normal PK activity. In view of the criticality normal PK activity has on healthy cell functioning, it is perhaps not surprising that abnormal PK activity has been related to a host of disorders, ranging from relatively non-life threatening diseases such as psoriasis to extremely virulent diseases such as glioblastoma (brain cancer).

Among other categorizations, PKs can be divided into two classes, the cytoplasmic protein tyrosine kinases (PTKs) and the transmembrane receptor tyrosine kinases (RTKs). Briefly, the RTKs comprise a family of transmembrane receptors with diverse biological activity. The HER subfamily of RTKs includes EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated alpha subunits and two beta subunits which cross the cell membrane and which contain the tyrosine kinase domain.

A third RTK subfamily is referred to as the "platelet derived growth factor receptor" ("PDGF-R") group, which includes PDGF-R-α, PDGF-R-β, CSFI-R, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group, which because of its similarity to the PDGF-R subfamily (and is sometimes subsumed into the PDGF-R subfamily) is the fetus liver kinase ("flk") receptor subfamily. This group is believed to be made up of kinase insert domain-receptor fetal liver kinase-1 (KDR/FLK-1, VEGF-R2), flk-1R, flk-4 and fms-like tyrosine kinase 1 (flt-1).

Still another member of the tyrosine kinase growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

Semaxanib is a potent and selective inhibitor of the Flk-1/KDR vascular endothelial growth factor (VEGF) receptor tyrosine kinase. It targets the VEGF pathway, and both in vivo and in vitro studies have demonstrated its antiangiogenic potential. Chemically, sunitinib's systematic name is "(3Z)-3-[(3,5-dimethyl-1H-pyrrol-2-yl)methylidene]-1,3-dihydro-2H-indol-2-one" and formula is provided below.

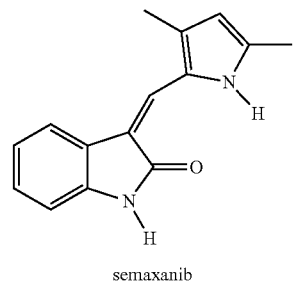 [SMILES: Cc1cc(C)c(/C=C2\C(=O)Nc3ccccc32)[nH]1]

semaxanib

Although initial testing with semaxanib was encouraging, a clinical trial associated with semaxanib showed that the drug did not achieve certain defined endpoints.

Therefore, a need exists to provide compounds that can exert the same pharmacology semaxanib in vivo, yet have properties different from semaxanib. The present invention seeks to address this and/or other needs.

SUMMARY

In one or more embodiments of the invention, a compound is provided, the compound comprising a semaxanib moiety residue covalently attached via a spacer moiety (e.g., a releasable linkage-containing spacer moiety) to a water-soluble, non-peptidic oligomer.

In one or more embodiments of the invention a compound is provided, the compound having the following

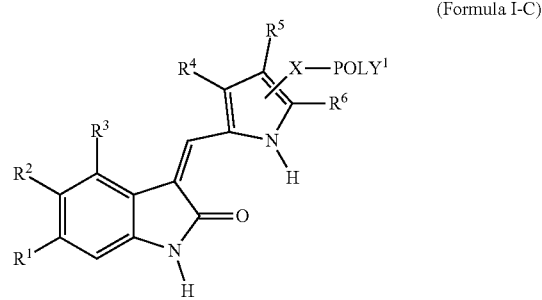

(Formula I-C)

wherein:

R¹ is selected from the group consisting of H and halo (e.g., F);

R² is selected from the group consisting of H, halo (e.g., F or Cl), $NO_2$ and lower alkyl (e.g., $CH_3$);

R³ is selected from the group consisting of H and lower alkyl (e.g., $CH_3$);

R⁴ is selected from the group consisting of H, halo (e.g., Br), lower alkyl (e.g., $CH_3$ and $CH_2CH_3$) and $CH_2CH_2COOH$;

R⁵ is selected from the group consisting of H, lower alkyl (e.g., $CH_3$ and $CH_2CH_3$), COOH, $CH_2CH_2COOCH_3$ and $COOCH_2CH_3$;

R⁶ is selected from the group consisting of H, halo (e.g., Br), lower alkyl ($CH_3$, $SCH_3$);

X is spacer moiety (which can be stable or be a releasable linkage-containing spacer moiety); and POLY¹ is a first water-soluble, non-peptidic polymer, and pharmaceutically acceptable salts thereof.

In one or more embodiments of the invention a compound is provided, the compound having the following

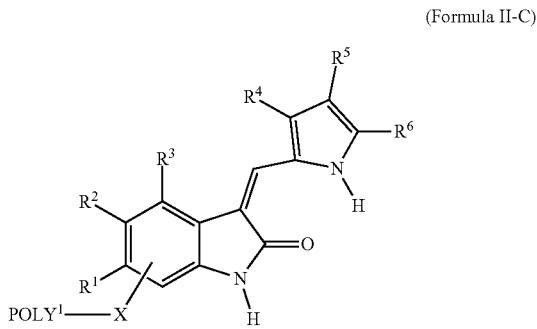

(Formula II-C)

wherein:

R¹ is selected from the group consisting of H and halo (e.g., F);

R² is selected from the group consisting of H, halo (e.g., F or Cl), $NO_2$ and lower alkyl (e.g., $CH_3$);

R³ is selected from the group consisting of H and lower alkyl (e.g., $CH_3$);

R⁴ is selected from the group consisting of H, halo (e.g., Br), lower alkyl (e.g., $CH_3$ and $CH_2CH_3$) and $CH_2CH_2COOH$;

R⁵ is selected from the group consisting of H, lower alkyl (e.g., $CH_3$ and $CH_2CH_3$), COOH, $CH_2CH_2COOCH_3$ and $COOCH_2CH_3$;

R⁶ is selected from the group consisting of H, halo (e.g., Br), lower alkyl ($CH_3$, $SCH_3$), X is spacer moiety (which can be stable or be a releasable linkage-containing spacer moiety); and POLY¹ is a first water-soluble, non-peptidic polymer, and and pharmaceutically acceptable salts thereof.

In one or more embodiments of the invention, a compound is provided, the compound having the following structure:

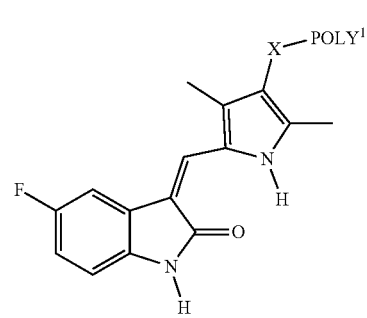

(Formula I-Ca)

wherein:

X is spacer moiety (which can be stable or be a releasable linkage-containing spacer moiety); and POLY¹ is a first water-soluble, non-peptidic polymer, and pharmaceutically acceptable salts thereof.

In one or more embodiments of the invention (containing two different attachment points for a water-soluble, non-peptidic polymer), a compound is provided, the compound having the following structure:

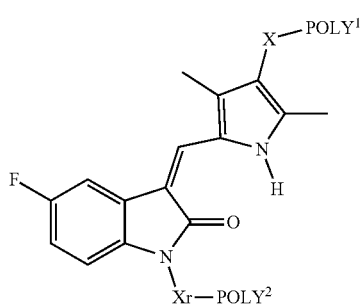

(Formula III-C)

wherein:

X is spacer moiety (which can be stable or be a releasable linkage-containing spacer moiety);

POLY¹ is a first water-soluble, non-peptidic polymer;

Xr is a releasable linkage-containing spacer moiety; and

POLY² is a second water-soluble, non-peptidic polymer, and pharmaceutically acceptable salts thereof.

In one or more embodiments of the invention (containing two different attachment points for a water-soluble, non-peptidic polymer), a compound is provided, the compound having the following structure:

(Formula IV-C)

wherein:

X is spacer moiety (which can be stable or be a releasable linkage-containing spacer moiety);

POLY[1] is a first water-soluble, non-peptidic polymer;
Xr is a releasable linkage-containing spacer moiety; and
POLY is a water-soluble, non-peptidic polymer,
and pharmaceutically acceptable salts thereof.

In one or more embodiments of the invention, a composition is provided, the composition comprising (i) a compound comprising a semaxanib moiety residue covalently attached via a releasable linkage-containing spacer moiety to a water-soluble, non-peptidic polymer, and, optionally, (ii) a pharmaceutically acceptable excipient.

In one or more embodiments of the invention, a dosage form is provided, the dosage form comprising a compound as described herein, wherein the compound is present in a dosage form.

In one or more embodiments of the invention, a method is provided, the method comprising covalently attaching a water-soluble, non-peptidic polymer to a semaxanib moiety.

In one or more embodiments of the invention, a method is provided, the method comprising administering a compound as described herein to a mammal in need thereof.

Additional embodiments of the present conjugates, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

DETAILED DESCRIPTION

Figure 1:
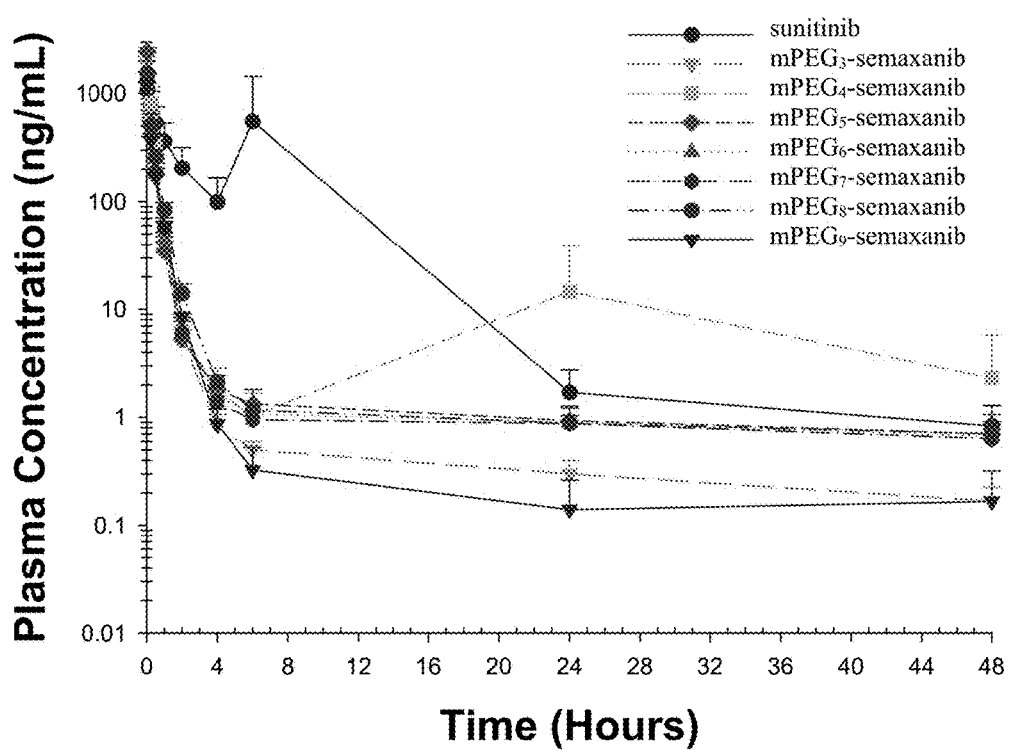
FIG. 1 is a plot of the mean plasma concentration values of sunitinib and mPEG$_{3-9}$-semaxanib compounds following 2 mg/kg intravenous dosing in rats, as further discussed in Example 4.

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic polymer" indicates an polymer that is at least 35% (by weight) soluble, preferably greater than 70% (by weight), and more preferably greater than 95% (by weight) soluble, in water at room temperature. Typically, an unfiltered aqueous preparation of a "water-soluble" polymer transmits at least 75%, more preferably at least 95%, of the amount of light transmitted by the same solution after filtering. It is most preferred, however, that the water-soluble polymer is at least 95% (by weight) soluble in water or completely soluble in water. With respect to being "non-peptidic," a polymer is non-peptidic when it has less than 35% (by weight) of amino acid residues.

The terms "monomer," "monomeric subunit" and "monomeric unit" are used interchangeably herein and refer to one of the basic structural units of a polymer. In the case of a homo-polymer, a single repeating structural unit forms the polymer. In the case of a co-polymer, two or more structural units are repeated—either in a pattern or randomly—to form the polymer. Preferred polymers used in connection with present the invention are homo-polymers. The water-soluble, non-peptidic polymer comprises one or more monomers serially attached to form a chain of monomers. The polymer can be formed from a single monomer type (i.e., is homo-polymeric) or two or three monomer types (i.e., is co-polymeric).

A "polymer" is a molecule possessing from about 2 to about 2000 or more (e.g., 2000 to 20000) monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG polymer" or any polyethylene glycol is one in which substantially all (preferably all) monomeric subunits are ethylene oxide subunits, though, the oligomer may contain distinct end capping moieties or functional groups, e.g., for conjugation. PEG polymers for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. As stated above, for the PEG polymers, the variable (n) ranges from about 2 to 2000 or more (e.g., 2000 to 20000), and the terminal groups and architecture of the overall PEG can vary. When PEG further comprises a functional group, A, for linking to, e.g., a small molecule drug, the functional group when covalently attached to a PEG oligomer does not result in formation of an oxygen-oxygen bond (—O—O—, a peroxide linkage).

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" is used herein to refer to a molecular structure that helps the conjugates of the invention to localize to a targeting area, e.g., help enter a cell, or bind a receptor. Preferably, the targeting moiety comprises a vitamin, antibody, antigen, receptor, DNA, RNA, sialyl Lewis X antigen, hyaluronic acid, sugars, cell-specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phosphatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Branched," in reference to the geometry or overall structure of a polymer, refers to a polymer having two or more polymers "arms" extending from a branch point.

"Forked," in reference to the geometry or overall structure of a polymer, refers to a polymer having two or more functional groups (typically through one or more atoms) extending from a branch point.

A "branch point" refers to a bifurcation point comprising one or more atoms at which a polymer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "releaseable linkage" is a relatively labile bond that cleaves under physiological conditions. An exemplary releasable linkage is a hydrolyzable bond that cleaves upon reaction with water (i.e., is hydrolyzed). The tendency of a bond to hydrolyze in water may depend not only on the general type of linkage connecting two atoms but also on the substituents attached to these atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates. Another exemplary releasable linkage is an enzymatically releasable linkage. An "enzymatically releasable linkage" means a linkage that is subject to cleavage by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, acyl, cyano. The substituted alkyl groups may be substituted once, twice or three times with the same or with different substituents.

"Lower alkyl" refers to an alkyl group containing from 1 to 7 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Pharmaceutically acceptable excipient" or "pharmaceutically acceptable carrier" refers to component that may be included in the compositions of the invention causes no significant adverse toxicological effects to a patient.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g., 1-2, 1-3 or 1-4 substituents) chosen from halo (F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

"Pharmacologically effective amount," "physiologically effective amount," and "therapeutically effective amount" are used interchangeably herein to mean the amount of a compound described herein that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A basic reactant or an acidic reactant described herein include neutral, charged, and any corresponding salt forms thereof.

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a semaxanib moiety residue covalently attached (either directly or through one or more atoms) to a water-soluble, non-peptidic polymer.

The semaxanib moiety residue is a residue of a semaxanib moiety. In one or more embodiments of the invention, the semaxanib moiety is encompassed by the following structure:

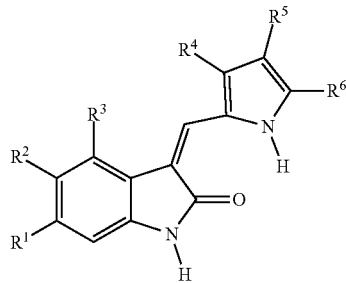

(Formula I)

wherein:
$R^1$ is selected from the group consisting of H and halo (e.g., F);
$R^2$ is selected from the group consisting of H, halo (e.g., F or Cl), $NO_2$ and lower alkyl (e.g., $CH_3$);
$R^3$ is selected from the group consisting of H and lower alkyl (e.g., $CH_3$);
$R^4$ is selected from the group consisting of H, halo (e.g., Br), lower alkyl (e.g., $CH_3$ and $CH_2CH_3$) and $CH_2CH_2COOH$;
$R^5$ is selected from the group consisting of H, lower alkyl (e.g., $CH_3$ and $CH_2CH_3$), COOH, $CH_2CH_2COOCH_3$ and $COOCH_2CH_3$; and $R^6$ is selected from the group consisting of H, halo (e.g., Br), lower alkyl ($CH_3$, $SCH_3$).

An exemplary semaxanib moiety is semaxanib (also referred to as "SU5416"), the chemical structure of which is provided above.

Semaxanib and other semaxanib moieties can be prepared in accordance with the procedures set forth in this disclosure as well as in Sun et al. (1998) *J. Med. Chem.* 41:2588-2603 and in U.S. Pat. Nos. 6,147,106, 6,610,688, 6,906,093, 6,908,930 and 7,202,265.

Exemplary compounds of the invention are encompassed by the following structure:

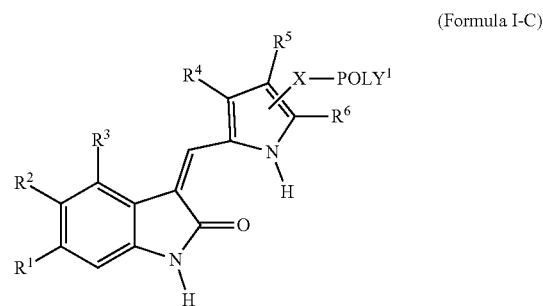

(Formula I-C)

wherein:
$R^1$ is selected from the group consisting of H and halo (e.g., F);
$R^2$ is selected from the group consisting of H, halo (e.g., F or Cl), $NO_2$ and lower alkyl (e.g., $CH_3$);
$R^3$ is selected from the group consisting of H and lower alkyl (e.g., $CH_3$);
$R^4$ is selected from the group consisting of H, halo (e.g., Br), lower alkyl (e.g., $CH_3$ and $CH_2CH_3$) and $CH_2CH_2COOH$;
$R^5$ is selected from the group consisting of H, lower alkyl (e.g., $CH_3$ and $CH_2CH_3$), COOH, $CH_2CH_2COOCH_3$ and $COOCH_2CH_3$; and
$R^6$ is selected from the group consisting of H, halo (e.g., Br), lower alkyl ($CH_3$, $SCH_3$),
and pharmaceutically acceptable salts thereof. It is understood that, with respect to the generic structure provided in Formula I-C, attachment of "~X-POLY$^1$" will take place at one of the $R^4$, $R^5$ and $R^6$ positions. Thus, for example, Formula I-Ca provides a generic structure in which attachment of "~X-POLY$^1$" occurs at the $R^5$ location.

Further exemplary compounds of the invention are encompassed by the following structure:

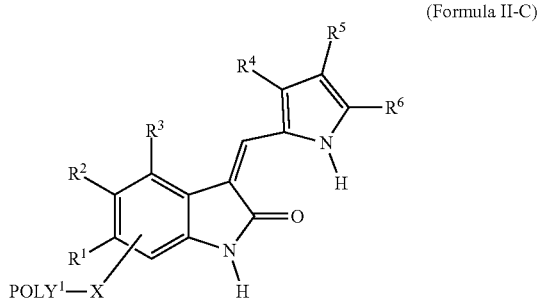

(Formula II-C)

wherein:
$R^1$ is selected from the group consisting of H and halo (e.g., F);

$R^2$ is selected from the group consisting of H, halo (e.g., F or Cl), $NO_2$ and lower alkyl (e.g., $CH_3$);

$R^3$ is selected from the group consisting of H and lower alkyl (e.g., $CH_3$);

$R^4$ is selected from the group consisting of H, halo (e.g., Br), lower alkyl (e.g., $CH_3$ and $CH_2CH_3$) and $CH_2CH_2COOH$;

$R^5$ is selected from the group consisting of H, lower alkyl (e.g., $CH_3$ and $CH_2CH_3$), COOH, $CH_2CH_2COOCH_3$ and $COOCH_2CH_3$; and $R^6$ is selected from the group consisting of H, halo (e.g., Br), lower alkyl ($CH_3$, $SCH_3$), and pharmaceutically acceptable salts thereof. It is understood that, with respect to the generic structure provided in Formula II-C, attachment of "~X-POLY$^1$" will take place at one of the available ring positions (e.g., $R^1$, $R^2$ and $R^3$ positions).

Still further exemplary compounds of the invention are encompassed by the following structure:

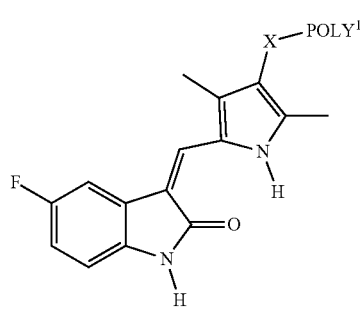

(Formula I-C)

wherein:
X is spacer moiety (which can be stable or be a releasable linkage-containing spacer moiety); and
POLY$^1$ is a first water-soluble, non-peptidic polymer, and pharmaceutically acceptable salts thereof.

Additional exemplary compounds of the invention are encompassed by the following structure:

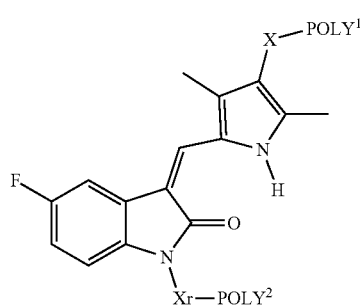

(Formula II-C)

wherein:
X is spacer moiety (which can be stable or be a releasable linkage-containing spacer moiety);
POLY$^1$ is a first water-soluble, non-peptidic polymer;
Xr is a releasable linkage-containing spacer moiety; and
POLY$^2$ is a second water-soluble, non-peptidic polymer, and pharmaceutically acceptable salts thereof. Approaches for providing attachment of ~Xr-POLY$^2$ can be found in U.S. Provisional Patent Application No. 61/426,919, filed on Dec. 23, 2010, and entitled "Polymer-Sunitinib Conjugates" (and the international patent application claiming priority thereto having the same title and filed on Dec. 23, 2011) and in U.S. Provisional Patent Application No. 61/426,893, filed on Dec. 23, 2010, and entitled "Polymer-Des-ethyl Sunitinib Conjugates" (and the international patent application claiming priority thereto having the same title and filed on Dec. 23, 2011).

Still more additional exemplary compounds of the invention are encompassed by the following structure:

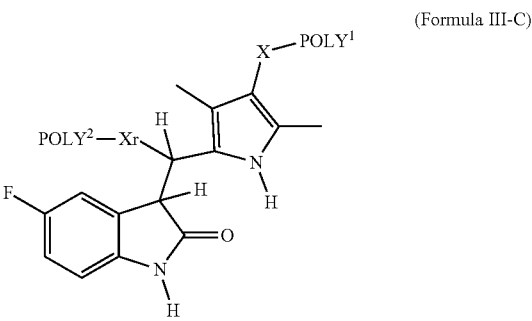

(Formula III-C)

wherein:
X is spacer moiety (which can be stable or be a releasable linkage-containing spacer moiety);
POLY$^1$ is a first water-soluble, non-peptidic polymer;
Xr is a releasable linkage-containing spacer moiety; and
POLY is a water-soluble, non-peptidic polymer,
and pharmaceutically acceptable salts thereof. Approaches for providing attachment of ~Xr-POLY$^2$ can be found in U.S. Provisional Patent Application No. 61/426,919, filed on Dec. 23, 2010, and entitled "Polymer-Sunitinib Conjugates" (and the international patent application claiming priority thereto having the same title and filed on Dec. 23, 2011) and in U.S. Provisional Patent Application No. 61/426,893, filed on Dec. 23, 2010, and entitled "Polymer-Des-ethyl Sunitinib Conjugates" (and the international patent application claiming priority thereto having the same title and filed on Dec. 23, 2011).

The Spacer Moiety

The spacer moiety (the linker through which the water-soluble, non-peptidic polymer is attached to the semaxanib moiety) may be a single bond, a single atom, such as an oxygen atom or a sulfur atom, two atoms, or a number of atoms. A spacer moiety is typically but is not necessarily linear in nature. In one or more embodiments, the spacer moiety, "X," is stable (and comprises no releasable linkages). In one or more embodiments, the spacer moiety, "X," comprises a releasable linkage. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—<u>NH</u>—<u>C</u>(O)—<u>NH</u>—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety, "X," may be any of the following: "-" (i.e., a covalent bond, that may be stable or degradable, between the substituted aromatic triazine residue and the water-soluble, non-peptidic oligomer), —O—, —NH—, —S—, —C(O)—, —C(O)O—, —OC(O)—, —CH₂—C(O)O—, —CH₂—OC(O)—, —C(O)O—CH₂—, —OC(O)—CH₂—, C(O)—NH, NH—C(O)—NH, O—C(O)—NH, —C(S)—, —CH₂—, —CH₂—CH₂—, —CH₂—CH₂—CH₂—, —CH₂—CH₂—CH₂—CH₂—, —O—CH₂—, —CH₂—O—, —O—CH₂—CH₂—, —CH₂—O—CH₂—, —CH₂—CH₂—O—, —O—CH₂—CH₂—CH₂—, —CH₂—O—CH₂—CH₂—, —CH₂—CH₂—O—CH₂—, —CH₂—CH₂—CH₂—O—, —O—CH₂—CH₂—CH₂—CH₂—, —CH₂—O—CH₂—CH₂—CH₂—, —CH₂—CH₂—O—CH₂—CH₂—, —CH₂—CH₂—CH₂—O—CH₂—, —CH₂—CH₂—CH₂—CH₂—O—, —C(O)—NH—CH₂—, —C(O)—NH—CH₂—CH₂—, —CH₂—C(O)—NH—CH₂—, —CH₂—CH₂—C(O)—NH—, —C(O)—NH—CH₂—CH₂—CH₂—, —CH₂—C(O)—NH—CH₂—CH₂—, —CH₂—CH₂—C(O)—NH—CH₂—, —CH₂—CH₂—CH₂—C(O)—NH—, —C(O)—NH—CH₂—CH₂—CH₂—CH₂—, —CH₂—C(O)—NH—CH₂—CH₂—CH₂—, —CH₂—CH₂—C(O)—NH—CH₂—CH₂—, —CH₂—CH₂—CH₂—C(O)—NH—CH₂—, —CH₂—CH₂—CH₂—CH₂—C(O)—NH—, —CH₂—CH₂—CH₂—CH₂—C(O)—NH—CH₂—CH₂—, —O—C(O)—NH—CH₂—, —CH₂—NH—C(O)—CH₂—, —CH₂—CH₂—NH—C(O)—CH₂—, —NH—C(O)—CH₂—CH₂—, —CH₂—NH—C(O)—CH₂—CH₂, —CH₂—CH₂—NH—C(O)—CH₂—CH₂, —C(O)—NH—CH₂—, —C(O)—NH—CH₂—CH₂—, —O—C(O)—NH—CH₂—, —O—C(O)—NH—CH₂—CH₂—, —NH—CH₂—, —NH—CH₂—CH₂—, —CH₂—NH—CH₂—, —CH₂—CH₂—NH—CH₂—, —C(O)—CH₂—, —C(O)—CH₂—CH₂—, —CH₂—C(O)—CH₂—, —CH₂—CH₂—C(O)— CH₂—, —CH₂—CH₂—C(O)—CH₂—CH₂—, —CH₂—CH₂—C(O)—, —CH₂—CH₂—CH₂—C(O)—NH—CH₂—C H₂—NH—, —CH₂—CH₂—CH₂—C(O)—NH—CH₂—CH₂—NH—C(O)—, —CH₂—CH₂—CH₂—C(O)—NH—CH₂—CH₂—NH—C(O)—CH₂—, bivalent cycloalkyl group, —N(R⁶)—, R⁶ is H or an organic radical selected from the group consisting of alkyl, substituted alkyl, alkenyl, substituted alkenyl, alkynyl, substituted alkynyl, aryl and substituted aryl. Additional spacer moieties include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, and guanidine. In some instances, a portion or a functional group of the drug compound may be modified or removed altogether to facilitate attachment of the oligomer. In some instances, it is preferred that X is not an amide, i.e., —CONR— and —RNCO—).

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The spacer moiety "X" between the water-soluble, non-peptidic polymer and the semaxanib moiety is formed by reaction of a functional group on a terminus of the polymer (or nascent polymer when it is desired to "grow" the polymer onto the semaxanib moiety) with a corresponding functional group within the semaxanib moiety. Illustrative reactions are described briefly below. For example, an amino group on a polymer may be reacted with a carboxylic acid or an activated carboxylic acid derivative on the semaxanib moiety, or vice versa, to produce an amide linkage. Alternatively, reaction of an amine on a polymer with an activated carbonate (e.g., succinimidyl or benzotriazolyl carbonate) on the semaxanib moiety, or vice versa, forms a carbamate linkage. Reaction of an amine on a polymer with an isocyanate (R—N=C=O) on a semaxanib, or vice versa, forms a urea linkage (R—NH—(C=O)—NH—R'). Further, reaction of an alcohol (alkoxide) group on a polymer with an alkyl halide, or halide group within a semaxanib moiety, or vice versa, forms an ether linkage. In yet another coupling approach, a small molecule having an aldehyde function is coupled to a polymer amino group by reductive amination, resulting in formation of a secondary amine linkage between the oligomer and the semaxanib.

A particularly preferred water-soluble, non-peptidic polymer is a polymer bearing an amine functional group. In this regard, the polymer will have the following structure: $CH_3O-(CH_2-CH_2O)_n-(CH_2)_p-NH_2$, wherein (n) is one of 1, 2, 3, 4, 5, 6, 7, 8, 9 and 10 and (p) is one of 1, 2, 3, 4, 5, 6 and 7. Preferred (n) values include 2, 3, 4 and 5 and preferred (p) values include 2, 3 and 4.

In one or more embodiments of the invention, a spacer moiety contained in the molecule is a releasable linkage-containing spacer moiety (e.g., "Xr" in each of Formulae II-C and III-C). A releasable linkage-containing spacer moiety must be one that will cleave in vivo following administration to a patient. In this regard, releasable linkages are known to those of ordinary skill in the art. In addition, whether a given linkage can serve as a releasable linkage in connection with the compounds provided herein can be tested through experimentation (e.g., by administering a compound having the proposed releasable linkage to a patient and testing, e.g., via chromatographic techniques, periodically obtained blood samples for indications of cleavage).

Exemplary releasable linkages for use in connection with the compounds provided herein include, without limitation, thioether, carbamate, ester, carbonate, urea and enzyme-cleavable peptidic linkages. Thioether, carbamate, ester, carbonate, urea can cleave via a (3-elimination reaction (with or without the enzymatic coordination, e.g., an ester can serve as a releaseable linkage herein regardless of whether the ester will be cleaved via an esterase). With respect to enzyme-cleavable peptidic linkages, the spacer moiety can include a series of amino acids known to be a substrate for an enzyme present in the intended patient population. In this way, upon administration to the patient, the enzyme-cleavable peptidic linkage-containing compound of the invention, will cleave the enzyme-cleavable peptidic linkage via enzymatic cleavage, thereby releasing semaxanib (or semaxanib with a relatively small molecular fragment). Examples of peptidic linkages subject to enzymatic cleavage in a given patient population have been described (see, for example, U.S. Patent Application Publication No. 2005/0079155) and can be determined experimentally.

In one or more embodiments of the invention, the releasable linkage-containing spacer moiety, "Xr," can take the following structure:

 (Formula III)

wherein:
(a) is either zero or one;
(b) is either zero or one;
$X^1$, when present, is a first spacer;

Lr is the releasable linkage; and

X², when present, is a second spacer.

In those instances of Formula III wherein both (a) and (b) are zero, it will be understood that the releasable linkage-containing spacer moiety is made up of only the releasable linkage. That is, the releasable linkage-containing spacer moiety only contains the releasable linkage and no other atoms are present between the semaxanib residue and the water-soluble, non-peptidic polymer.

In those instances of Formula III wherein either or both of (a) and (b) are one, it will be understood that the releasable linkage-containing spacer moiety contains one or more additional atoms other than those that make up the releasable linkage. Nonlimiting exemplary spacers (e.g., $X^1$ and $X^2$) that may flank the releasable linkage include —O—, —NH—, —S—, —C(O)—, —C(O)O—, —OC(O)—, —CH₂—C(O)O—, —CH₂—OC(O)—, —C(O)O—CH₂—, —OC(O)—CH₂—, C(O)—NH, NH—C(O)—NH, O—C(O)—NH, —C(S)—, —CH₂—, —CH₂—CH₂—, —CH₂—CH₂—CH₂—, —CH₂—CH₂—CH₂—CH₂—, —O—CH₂—, —CH₂—O—, —O—CH₂—CH₂—, —CH₂—O—CH₂—, —CH₂—CH₂—O—, —O—CH₂—CH₂—CH₂—, —CH₂—O—CH₂—CH₂—, —CH₂—CH₂—O—CH₂—, —CH₂—CH₂—CH₂—O—, —O—CH₂—CH₂—CH₂—CH₂—, —CH₂—O—CH₂—CH₂—CH₂—, —CH₂—CH₂—O—CH₂—CH₂—, —CH₂—CH₂—CH₂—O—CH₂—, —CH₂—CH₂—CH₂—CH₂—O—, —C(O)—NH—CH₂—, —C(O)—NH—CH₂—CH₂—, —CH₂—C(O)—NH—CH₂—, —CH₂—CH₂—C(O)—NH—, —C(O)—NH—CH₂—CH₂—CH₂—, —CH₂—C(O)—NH—CH₂—CH₂—, —CH₂—CH₂—C(O)—NH—CH₂—, —CH₂—CH₂—CH₂—C(O)—NH—, —C(O)—NH—CH₂—CH₂—CH₂—CH₂—, —CH₂—C(O)—NH—CH₂—CH₂—CH₂—, —CH₂—CH₂—C(O)—NH—CH₂—CH₂—, —CH₂—CH₂—CH₂—C(O)—NH—CH₂—, —CH₂—CH₂—CH₂—CH₂—C(O)—NH—, —CH₂—CH₂—CH₂—CH₂—C(O)—NH—NH—C(O)—CH₂—, —CH₂—NH—C(O)—CH₂—, —CH₂—CH₂—NH—C(O)—CH₂—, —NH—C(O)—CH₂—CH₂—, —CH₂—NH—C(O)—CH₂—CH₂, —CH₂—CH₂—NH—C(O)—CH₂—CH₂, —C(O)—NH—CH₂—, —C(O)—NH—CH₂—CH₂—, —O—C(O)—NH—CH₂—, —O—C(O)—NH—CH₂—CH₂—, —NH—CH₂—, —NH—CH₂—CH₂—, —CH₂—NH—CH₂—, —CH₂—CH₂—NH—CH₂—, —C(O)—CH₂—, —C(O)—CH₂—CH₂—, —CH₂—C(O)—CH₂—, —CH₂—CH₂—C(O)—CH₂—, —CH₂—CH₂—C(O)—CH₂—CH₂—, —CH₂—CH₂—C(O)—, —CH₂—CH₂—CH₂—C(O)—NH—CH₂—CH₂—NH—, —CH₂—CH₂—CH₂—C(O)—NH—CH₂—CH₂—NH—C(O)—, —CH₂—CH₂—CH₂—C(O)—NH—CH₂—CH₂—NH—C(O)—CH₂—, bivalent cycloalkyl group, —N(R⁶)—, R⁶ is H or an organic radical selected from the group consisting of alkyl, substituted alkyl, alkenyl, substituted alkenyl, alkynyl, substituted alkynyl, aryl and substituted aryl. Additional spacers include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, fluorenyl, and guanidine. For purposes of the present invention, however, a group of atoms is not considered a spacer when it is immediately adjacent to an polymeric segment, and the group of atoms is the same as a monomer of the polymer such that the group would represent a mere extension of the polymer chain.

When present, a spacer is typically but is not necessarily linear in nature. In addition, a spacer is typically but is not necessarily hydrolytically stable and/or is enzymatically stable. In one or more embodiments of the invention, the spacer, when present, has a chain length of less than about 12 atoms (e.g., less than about 10 atoms, less than about 8 atoms, and less than about 5 atoms). With respect to determining length of a particular spacer, length herein is defined as the number of atoms in a single chain, not counting substituents. For instance, a urea linkage such as this, $R_{polymer}$—NH—(C=O)—NH—$R'_{drug}$, is considered to have a chain length of three atoms (—N̲H—C̲(O)—N̲H—).

The Water-Soluble, Non-Peptidic Polymer, "POLY¹", "POLY²," and so Forth

The compounds of the invention include a water-soluble, non-peptidic polymer. A wade array of polymers can be used and the invention is not limited with respect to the type (e.g., polyethylene oxide, polyoxazoline, and so forth), size (e.g., from 2 to 4000 monomers in size) and geometry (e.g., linear, branched, multi-armed, and so forth) used.

With respect to type, the water-soluble, non-peptidic polymer can be understood as a series of repeating monomers, wherein the type of monomer(s) dictates the type of water-soluble, non-peptidic polymer. Exemplary monomers include, but are not limited to the group consisting of: alkylene oxides, such as ethylene oxide or propylene oxide; olefinic alcohols, such as vinyl alcohol, 1-propenol or 2-propenol; vinyl pyrrolidone; hydroxyalkyl methacrylamide and hydroxyalkyl methacrylate, where, in each case, alkyl is preferably methyl; α-hydroxy acids, such as lactic acid or glycolic acid; phosphazene, oxazoline, carbohydrates such as monosaccharides, alditol such as mannitol; and N-acryloylmorpholine. In one or more embodiments, the water-soluble, non-peptidic polymer is a co-polymer of two monomer types selected from this group, or, more preferably, is a homo-polymer of one monomer type selected from this group. With respect to co-polymers, the two monomer types in a co-oligomer may be of the same monomer type, for example, two alkylene oxides, such as ethylene oxide and propylene oxide.

With respect to size, the water-soluble, non-peptidic polymer can be a relatively small or the water-soluble, non-peptidic polymer can be relatively large.

In those embodiments in which a relatively small water-soluble, non-peptidic polymer is present, exemplary values of molecular weights include: below about 2000; below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons. Exemplary ranges for a relatively small water-soluble, non-peptidic polymer include from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

For relatively small water-soluble, non-peptidic polymers, the number of monomers in will typically fall within one or more of the following ranges: between 1 and about 30 (inclusive); between about 2 and about 25; between about 2 and about 20; between about 2 and about 15; between about 2 and about 12; between about 2 and about 10. In certain instances, the number of monomers in series in the polymer (and the corresponding conjugate) is one of 1, 2, 3, 4, 5, 6, 7, or 8. In additional embodiments, the polymer (and the corresponding conjugate) contains 9, 10, 11, 12, 13, 14, 15, 16, 17, 18, 19, or 20 monomers. In yet further embodiments, the polymer (and the corresponding conjugate) possesses 21, 22, 23, 24, 25, 26, 27, 28, 29 or 30 monomers in series. Thus, for example, when the water-soluble, non-peptidic polymer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic polymer has 1, 2, 3, 4, 5, 6, 7, 8, 9, or 10 monomers, these values correspond to a methoxy end-capped poly(ethylene oxide) having a molecular weights of about 75, 119, 163, 207, 251, 295, 339, 383, 427, and 471 Daltons, respectively. When the polymer has 11, 12, 13, 14, or 15 monomers, these values correspond to methoxy end-capped poly(ethylene oxide) having molecular weights corresponding to about 515, 559, 603, 647, and 691 Daltons, respectively.

When the molecular weight of the water-soluble, non-peptidic polymer in the compound is relatively large (e.g., greater than 2,000 Daltons), the weight can fall within the range of 2,000 Daltons to about 150,000 Daltons. Exemplary ranges, however, include molecular weights in the range of from about 3,000 Daltons to about 120,000 Daltons; in the range of from about 5,000 Daltons to about 110,000 Daltons; in the range of from greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons.

Exemplary molecular weights for relatively large water-soluble, non-peptidic polymers include about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble, non-peptidic polymer (e.g., a branched 40,000 Dalton water-soluble polymer comprised of two 20,000 Dalton polymers) and multi-arm versions of the water-soluble, non-peptidic polymer (e.g., a four-armed 40,000 Dalton water-soluble polymer comprised of four 10,000 Dalton polymers) having a total molecular weight of any of the foregoing can also be used.

Thus, regardless of whether a relatively small or large water-soluble, non-peptidic polymer is used, when the water-soluble, non-peptidic polymer is a poly(ethylene oxide), the polymer will comprise a number of $(OCH_2CH_2)$ monomers [or $(CH_2CH_2O)$ monomers, depending on how the PEG is defined]. As used throughout the description, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

With respect to geometry, any geometry (e.g., linear, branched, multi-armed) can be used in connection with the conjugates of the invention and the invention is not limited in this regard.

With respect to linear water-soluble, non-peptidic polymers, typically, although not necessarily, a linear water-soluble, non-peptidic polymer will be terminally end capped with a substantially inert group (e.g., with a methyl or methoxy group) on the terminus not attached to releasable linkage-containing spacer moiety. In one or more embodiments, however, compounds of invention having a linear, water-soluble, non-peptidic polymer will not be terminally end capped with a substantially inert group and will instead have a functional group. In such embodiments, the linear, water-soluble, non-peptidic polymer can afford compounds of the invention having two semaxanib moiety residues attached to it. In another form of such embodiments, the linear, water-soluble, non-peptidic polymer can afford compounds of the invention having a single semaxanib moiety residue and a residue of a different moiety (e.g., a targeting moiety).

With respect to branched water-soluble, non-peptidic polymers, these polymers typically contain a two discernable end capped water-soluble, non-peptidic polymers connected via a branch point, which is connected through a spacer to either a functional group (prior to conjugation) or semaxanib moiety residue. Exemplary branched forms of water-soluble, non-peptidic polymers are described herein and in WO 2005/107815, WO 2005/108463, U.S. Pat. Nos. 5,932,462 and 7,026,440, and U.S. Patent Application Publication No. 2005/0009988. Among other benefits, branched water-soluble, non-peptidic polymers—given the presence of two discernable water-soluble, non-peptidic polymers—have the potential to provide greater polymer character compared to, for example, a linear polymer having a single water-soluble, non-peptidic polymer.

As used herein, reference to a "water-soluble, non-peptidic polymer" (e.g., "POLY") is considered to include branched and multi-arm forms even though two or more discernable water-soluble, non-peptidic polymers can be identified.

With respect to multi-arm water-soluble, non-peptidic polymers, these polymers typically contain three or more discernable water-soluble, non-peptidic polymers, each having the ability to covalently attach to a moiety of interest, and each typically connected to a central core moiety (e.g., a residue of a polyol). Among other benefits, multi-arm water-soluble, non-peptidic polymers—given the ability of each arm to covalently attach to a drug—have the potential to provide greater drug character compared to, for example, a linear polymer having a single drug attached thereto.

Methods for Synthesizing Compounds of the Invention

The compounds discussed herein can be prepared in a variety of methods and the invention is not limited in this regard.

In one or more embodiments, the compounds of the prepared by a method comprising covalently attaching a water-soluble, non-peptidic polymer to a semaxanib moiety.

With respect to the water-soluble, non-peptidic polymer, such polymers can be obtained commercially in a form bearing one or more reactive groups, thereby providing a reagent suited for facile covalent attachment to the semaxanib moiety. In this form, the water-soluble, non-peptidic polymer is sometimes conventionally referred to as a polymeric reagent. Commercial suppliers for polymeric reagents include Sigma-Aldrich (St. Louis, Mo.), Creative PEG-Works (Winston Salem, N.C. USA), SunBio PEG-Shop (SunBio USA, Orinda, Calif.), JenKem Technology USA (Allen, Tex.), and NOF America Corporation (White Plains, N.Y.). Using routine experimentation, one of ordinary skill in the art can identify polymeric reagents having suitable sizes, geometries, and reactive groups and so forth for preparing the compounds of the invention. For example, it is possible to prepare a series of compounds wherein each member in the series differs in a feature (e.g., the size of the water-soluble, non-peptidic polymer, the type of reactive group, the ability of a linkage to release, and so forth) and then administer one member in the series to a patient followed by periodic detection and quantification (e.g., using chromatographic techniques) of the compound (and/or metabolite thereof) in blood and/or urine samples along with the assessment of a clinical endpoint. Each member of the series is administered, quantified and assessed in a similar way to a naïve patient. Once each members of the series is tested, the results can be reviewed to determine which feature(s) provided compounds having the desired effect(s).

Covalently attaching the polymeric reagent to the semaxanib moiety is typically conducted under conjugation conditions, which conditions include combining the semaxanib moiety with a polymeric reagent (often a molar excess of polymeric reagent relative to the semaxanib moiety) under conditions of temperature, pH, time and solvent that allow for covalent attachment between a reactive group of the polymeric reagent to the semaxanib moiety.

Exemplary conjugation conditions between a given polymeric reagent bearing a reactive group and the semaxanib moiety will be known to one of ordinary skill in the art based upon the disclosure provided herein and in the context of the relevant literature. See, for example, *Poly(ethylene glycol) Chemistry and Biological Applications*, American Chemical Society, Washington, D.C. (1997).

Exemplary linear, branched and multi-armed polymeric reagents (along with exemplary conjugation conditions for those polymeric reagents) along with the releasable linkage-containing compounds formed therefrom are provided in U.S. Provisional Patent Application No. 61/426,919, filed on Dec. 23, 2011, and entitled "Polymer-Sunitinib Conjugates" and in U.S. Provisional Patent Application No. 61/426,893, filed on Dec. 23, 2011, and entitled "Polymer-Des-ethyl Sunitinib Conjugates." Utility and Testing of Compounds.

Animal models (rodents and dogs) can used to study oral drug transport. In addition, non-in vivo methods include rodent everted gut excised tissue and Caco-2 cell monolayer tissue-culture models. These models are useful in predicting oral drug bioavailability (thereby providing an indication of whether a given compound of the invention can be administered orally).

To test for binding activity, a compound can be tested using in vitro binding studies to receptors using various cell lines expressing these receptors. In vitro binding studies known to those of ordinary skill in the art can be used to test the binding for a receptor of interest.

The following assay may be used to determine the level of activity and effect of a compound on protein kinases. The assay is performed in an ELISA (Enzyme-Linked Immunosorbent Sandwich Assay) format [Voller et al. (1980), "Enzyme-Linked Immunosorbent Assay," Manual of Clinical Immunology, 2d ed., Rose and Friedman, *Am. Soc. Of Microbiology*, Washington, D.C., pp. 359-371]. The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound. Similar assays can be designed along the same lines for any protein kinase using techniques well known in the art.

Using this basic approach, one can test over 80 protein kinases, including GST-Flk1, pyk2, PYK2, FGFR-1R, EGFR, PDGFR, HER-2, CDK2, and IGF-1.

The compounds of the invention may be tested in animal models of cancers to determine their cancer-inhibition potential. An exemplary model is the xenograft-based assay. In this assay, the ability of human tumors to grow as xenografts in athymic mice (e.g., Balb/c, nu/nu) provides a useful in vivo model for studying the biological response to therapies for human tumors. Since the first successful xenotransplantation of human tumors into athymic mice [Rygaard et al. (1969) *Acta Pathol. Microbial. Scand.* 77:758-760), many different human tumor cell lines (e.g., mammary, lung, genitourinary, gastro-intestinal, head and neck, glioblastoma, bone, and malignant melanomas) have been transplanted and successfully grown in nude mice.

In addition to an approach as provided in the Experimental, the following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a tyrosine kinase to phosphorylate tyrosines on a known substrate in a cell. The object of the cellular/biological assays is to determine the effect of a compound on the biological response stimulated by a tyrosine kinase in a cell. The object of the in vivo assays is to determine the effect of a compound in an animal model of a particular disorder such as cancer.

Suitable cell lines for subcutaneous xenograft experiments include C6 cells (glioma, ATCC #CCL 107), A375 cells (melanoma, ATCC #CRL 1619), A431 cells (epidermoid carcinoma, ATCC #CRL 1555), Calu 6 cells (lung, ATCC #HTB 56), PC3 cells (prostate, ATCC #CRL 1435), SKOV3TP5 cells and NIH 3T3 fibroblasts genetically engineered to overexpress EGFR, PDGFR, IGF-1R or any other test kinase. The following protocol can be used to perform xenograft experiments.

Female athymic mice (BALB/c, nu/nu) are maintained under clean-room conditions in micro-isolator cages with Alpha-dri bedding. They receive sterile rodent chow and water ad libitum.

Cell lines are grown in appropriate medium [for example, MEM, DMEM, Ham's F10, or Ham's F12 plus 5%-10% fetal bovine serum (FBS) and 2 mM glutamine (GLN)]. All cells are grown in a humid atmosphere of 90-95% air and 5-10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for ten minutes. Pellets are resuspended in sterile PBS or media (without FBS) to a particular concentration and the cells are implanted into the hindflank of the mice (8-10 mice per group, $2\text{-}10 \times 10^6$ cells/animal). Tumor growth is measured over 3 to 6 weeks using venier calipers. Tumor volumes are calculated as a product of length×width×height. P values are calculated using the Students t-test. Test compounds in 50-100 µL excipient (DMSO, or VPD:DSW) can be delivered by IP injection at different concentrations generally starting at day one after implantation.

The compounds of the invention may be administered per se or in the form of a pharmaceutically acceptable salt, and any reference to the compounds of the invention herein is intended to include pharmaceutically acceptable salts. If used, a salt of a compound as described herein should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the compound with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulfonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

The compounds of the invention may contain one or more chiral centers and for each chiral center, the invention contemplates each optical isomer as well as any combination or ratio of or an optically active form, for example, a single optically active enantiomer, or any combination or ratio of enantiomers (e.g., scalemic and racemic mixtures). In addition, the small molecule drug may possess one or more geometric isomers. With respect to geometric isomers, a composition can comprise a single geometric isomer or a mixture of two or more geometric isomers.

The present invention also includes pharmaceutical preparations comprising a compound as provided herein in combination with a pharmaceutical excipient. Generally, the compound itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which can be in the form of a powder or cake), as well as formulations prepared for injection, which are liquid and require the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, normally being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compounds of the invention can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The compounds of the invention can also be formulated into a suppository for rectal administration. With respect to suppositories, the compound is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the compound (either before or after melting of the suppository base material); pouring the melt into a mold; cooling the melt (e.g., placing the melt-containing mold in a room temperature environment) to thereby form suppositories; and removing the suppositories from the mold.

In some embodiments of the invention, the compositions comprising the compounds of the invention may further be incorporated into a suitable delivery vehicle. Such delivery vehicles may provide controlled and/or continuous release of the compounds and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodoto-*

*rula* yeast cell particles (YCP). Yeast cells such as *S. cerevisiae* and *Rhodotorula* species are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495, 4,810,646, 4,992,540, 5,028,703, 5,607,677 and U.S. Patent Application Publication Nos. 2005/0281781 and 2008/0044438.

The invention also provides a method for administering a compound of the invention as provided herein to a patient suffering from a condition that is responsive to treatment with the compound. The method comprises administering, generally orally, a therapeutically effective amount of the compound (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

In one or more embodiments of the invention, a method is provided, the method being directed to a method of treating diseases mediated by abnormal protein kinase activity, in particular, receptor tyrosine kinases (RTKs), non-receptor protein tyrosine kinases (CTKs) and serine/threonine protein kinases (STKs), in a patient, in particular humans, which method comprises administering to said patient a pharmaceutical composition comprising a compound of the invention as described herein. Such diseases include, by way of example and not limitation, cancer, diabetes, hepatic cirrhosis, cardiovasacular disease such as atherosclerosis, angiogenesis, immunological disease such as autoimmune disease and renal disease.

In one or more embodiments of the invention, the invention is directed to the use of a compound of the invention as described herein in the preparation of a medicament which is useful in the treatment of a disease mediated by abnormal PK activity.

The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given compound of the invention (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents, patent applications, patent publications and references identified herein are incorporated by reference in their entireties. In the event of an inconsistency between the teachings of this specification and the art incorporated by reference, the meaning of the teachings in this specification shall prevail.

EXAMPLES

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All non-PEG chemical reagents referred to in the appended examples are commercially available unless otherwise indicated. The preparation of PEG-mers is described in, for example, U.S. Patent Application Publication No. 2005/0136031.

$^1$H NMR (nuclear magnetic resonance) data was generated by an NMR spectrometer. A list of certain compounds as well as the source of the compounds is provided below.

Example 1

Synthesis of (Z)-5-((5-fluoro-2-oxoindolin-3-ylidene)methyl)-2,4-dimethyl-1H-pyrrole-3-mPEG$_n$-amide A series of mPEGn-semaxanib conjugates were prepared, each conjugate having a different molecule weight. Schematically, the synthetic approach followed to prepare the conjugates in this series is provided below.

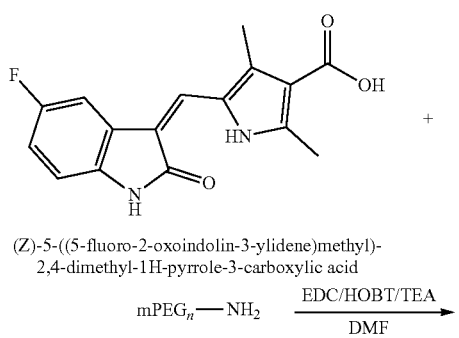

(Z)-5-((5-fluoro-2-oxoindolin-3-ylidene)methyl)-2,4-dimethyl-1H-pyrrole-3-carboxylic acid mPEG$_n$—NH$_2$ $\xrightarrow{\text{EDC/HOBT/TEA}}{\text{DMF}}$

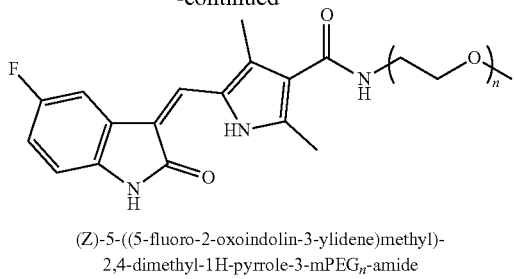

(Z)-5-((5-fluoro-2-oxoindolin-3-ylidene)methyl)-
2,4-dimethyl-1H-pyrrole-3-mPEG$_n$-amide n = 3-9

For each conjugate in the series, the synthesis was completed in the dark due to the light sensitivity of the materials. A similar synthetic approach was followed seven times, one for each of mPEG$_n$-NH$_2$ wherein n=3 through 9. Generally, the (Z)-5-((5-fluoro-2-oxoindolin-3-ylidene)methyl)-2,4-dimethyl-1H-pyrrole-3-carboxylic acid (300 mg, 1.0 mmol) (obtained commercially) dissolved in 20 mL dimethylformamide (DMF) which resulted in a cloudy yellow solution. Then, triethanolamine (TEA) (276 mg, 2.8 mmol) was added and the solution turned clear yellow. N-Hydroxybenzotriazole (HOBT) (162 mg, 1.2 mmol) and 1-ethyl-3-(3-dimethylaminopropyl) carbodiimide (EDC) (960 mg, 5.0 mmol) were added to the reaction mixture. After all reactants were completely dissolved, mPEG$_n$-NH$_2$ (1.2 mmol) was added. After two hours the reaction was complete (checked by HPLC). Then, 150 mL of dichloromethane (DCM) was added to the reaction mixture. The organic phase was washed with 5% NaHCO$_3$ (100 mL) and water (150 mL×3). The organic phase was dried over sodium sulfate and solvent was removed under reduced pressure. The yellow oil obtained was purified by Biotage flash chromatography on silica gel (2-8% MeOH in DCM in 23 CV, 40M column). The desired product was obtained as a yellow solid. (Yield 38%-66%). The NMR data associated with each synthesis of n=3 through 9 for mPEG$_n$-NH$_2$ is provided below.

(Z)-5-((5-fluoro-2-oxoindolin-3-ylidene)methyl)-2,4-dimethyl-1H-pyrrole-3-mPEG$_3$-amide ("mPEG$_3$-semaxanib"): $^1$H-NMR (500 MHz, CDCl$_3$) □□δ 7.95 (s, 1H), 7.35 (s, 1H), 7.19 (d, 1H), 6.86 (m, 2H), 6.27 (s, 1H), 3.73-3.65 (m, 10H), 3.54 (m, 2H), 3.34 (s, 3H), 2.58 (s, 3H), 2.47 (s, 3H) LC-MS: Calc. 445.2; Found, 446.2 (MH$^+$). Molecular weight=445.2.

(Z)-5-((5-fluoro-2-oxoindolin-3-ylidene)methyl)-2,4-dimethyl-1H-pyrrole-3-mPEG$_4$-amide ("mPEG$_4$-semaxanib"): $^1$H-NMR (500 MHz, CDCl$_3$) □δ 7.85 (s, 1H), 7.29 (s, 1H), 7.15 (d, 1H), 6.80 (m, 2H), 6.26 (s, 1H), 3.75-3.50 (m, 14H), 3.49 (m, 2H), 3.30 (s, 3H), 2.47 (s, 3H), 2.36 (s, 3H) LC-MS: Calc. 489.2; Found, 490.2 (MH$^+$). Molecular weight=489.2.

(Z)-5-((5-fluoro-2-oxoindolin-3-ylidene)methyl)-2,4-dimethyl-1H-pyrrole-3-mPEG$_5$-amide ("mPEG$_5$-semaxanib"): $^1$H-NMR (500 MHz, CDCl$_3$) δ 8.15 (s, 1H), 7.24 (s, 1H), 7.10 (d, 1H), 6.75 (m, 2H), 6.30 (s, 1H), 3.62-3.56 (m, 18H), 3.53 (m, 2H), 3.28 (s, 3H), 2.47 (s, 3H), 2.36 (s, 3H) LC-MS: Calc. 533.2; Found, 534.2 (MH$^+$). Molecular weight=533.2.

(Z)-5-((5-fluoro-2-oxoindolin-3-ylidene)methyl)-2,4-dimethyl-1H-pyrrole-3-mPEG$_6$-amide ("mPEG$_6$-semaxanib"): $^1$H-NMR (500 MHz, CDCl$_3$) δ 8.11 (s, 1H), 7.33 (s, 1H), 7.18 (d, 1H), 6.85 (m, 2H), 6.30 (s, 1H), 3.71-3.64 (m, 22H), 3.55 (m, 2H), 3.38 (s, 3H), 2.56 (s, 3H), 2.45 (s, 3H) LC-MS: Calc. 577.2; Found, 578.2 (MH$^+$). Molecular weight=577.2.

(Z)-5-((5-fluoro-2-oxoindolin-3-ylidene)methyl)-2,4-dimethyl-1H-pyrrole-3-mPEG$_7$-amide ("mPEG$_7$-semaxanib"): $^1$H-NMR (500 MHz, CDCl$_3$) δ 8.11 (s, 1H), 7.26 (s, 1H), 7.15 (d, 1H), 6.77 (m, 2H), 6.26 (s, 1H), 3.63-3.57 (m, 28H), 3.30 (s, 3H), 2.49 (s, 3H), 2.38 (s, 3H) LC-MS: Calc. 621.3; Found, 622.4 (MH$^+$). Molecular weight=621.3.

(Z)-5-((5-fluoro-2-oxoindolin-3-ylidene)methyl)-2,4-dimethyl-1H-pyrrole-3-mPEG$_8$-amide ("mPEG$_8$-semaxanib"): $^1$H-NMR (500 MHz, CDCl$_3$) □δ 7.95 (s, 1H), 7.31 (s, 1H), 7.15 (d, 1H), 6.77 (m, 2H), 6.25 (s, 1H), 3.61-3.54 (m, 32H), 3.31 (s, 3H), 2.50 (s, 3H), 2.41 (s, 3H) LC-MS: Calc. 665.3; Found, 666.4 (MH$^+$). Molecular weight=665.3.

(Z)-5-((5-fluoro-2-oxoindolin-3-ylidene)methyl)-2,4-dimethyl-1H-pyrrole-3-mPEG$_8$-amide ("mPEG$_9$-semaxanib"): $^1$H-NMR (500 MHz, CDCl$_3$) □ 1H) δ 8.11 (s, 1H), 7.32 (s, 1H), 7.15 (d, 1H), 6.77 (m, 2H), 6.28 (s, 1H), 3.61-3.54 (m, 36H), 3.48 (s, 3H), 2.50 (s, 3H), 2.40 (s, 3H) LC-MS: Calc. 709.3; Found, 710.5 (MH$^+$). Molecular weight=709.3.

Example 2

In Vitro Activity of mPEG$_n$-Semaxanib and Sunitinib c-Kit tyrosine kinase inhibition mPEG$_n$-semaxanib (prepared as described in Example 1, n=3-9) and the known tyrosine kinase inhibitor, sunitinib (free base) (obtained commercially as the malate salt, but subsequently isolated) were determined.

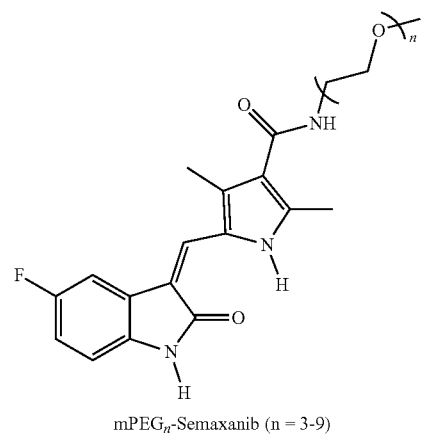

mPEG$_n$-Semaxanib (n = 3-9)

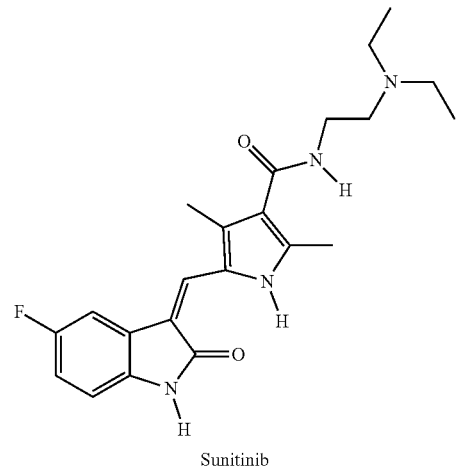

Sunitinib

Using a commercially available screening approach (Caliper Technologies, Mountain View, Calif.), mPEG$_n$-semaxanib (n=3-9) and sunitinib were tested for activity to determine their IC50 values against three targets. Briefly, the screening approach measures the conversion of a fluorescent substrate to a phosphorylated product. The reaction mixture, from a microtiter plate well, is introduced through a capillary sipper onto the chip, where the nonphosphorylated substrate and phosphorylated product are separated by electrophoresis and detected via laser-induced fluorescence. The signature of the fluorescence signal over time reveals the extent of the reaction.

Results shown are the averages of replicate wells. Table 1 provides c-Kit results, Table 2 provides VEGFR-2 results and Table 3 provides RET results. A result of >3E-06 is reported for curves that did not reach 50% activity at the highest concentration chosen for the study. Activity must be ≤50% to report an accurate IC50.

TABLE 1 c-Kit AVG % Activity at Specific Concentration

| Compound ID | 3.0E−05 | 1.0E−05 | 3.0E−06 | 1.0E−06 | 3.0E−07 | 1.0E−07 | 3.0E−08 |
|---|---|---|---|---|---|---|---|
| sunitinib malate | 0 | −1 | 0 | 0 | 6 | 38 | 81 |
| mPEG$_3$-semaxanib | −1 | −1 | 1 | 2 | 16 | 58 | 88 |
| mPEG$_4$-semaxanib | −1 | −1 | −1 | 3 | 24 | 70 | 94 |
| mPEG$_5$-semaxanib | −1 | −1 | 0 | 6 | 37 | 76 | 96 |
| mPEG$_6$-semaxanib | −1 | −1 | 0 | 8 | 44 | 79 | 95 |
| mPEG$_7$-semaxanib | −1 | −1 | 1 | 11 | 49 | 82 | 96 |
| mPEG$_8$-semaxanib | −1 | −1 | 1 | 11 | 49 | 75 | 93 |
| mPEG$_9$-semaxanib | −1 | 0 | 2 | 16 | 60 | 90 | 100 |

| Compound ID | 1.0E−08 | 3.0E−09 | 1.0E−09 | 3.0E−10 | 1.0E−10 | IC50 (nM) | Fold |
|---|---|---|---|---|---|---|---|
| sunitinib malate | 91 | 100 | 103 | 100 | 102 | 73.00 | |
| mPEG$_3$-semaxanib | 97 | 98 | 104 | 102 | 100 | 120.00 | 1.60 |
| mPEG$_4$-semaxanib | 97 | 93 | 99 | 100 | 97 | 170.00 | 2.30 |
| mPEG$_5$-semaxanib | 106 | 99 | 100 | 99 | 90 | 230.00 | 3.10 |
| mPEG$_6$-semaxanib | 94 | 99 | 97 | 87 | 91 | 290.00 | 3.90 |
| mPEG$_7$-semaxanib | 96 | 98 | 97 | 96 | 97 | 320.00 | 4.30 |
| mPEG$_8$-semaxanib | 97 | 98 | 98 | 94 | 94 | 300.00 | 4.10 |
| mPEG$_9$-semaxanib | 102 | 105 | 105 | 102 | 95 | 390.00 | 5.30 |

TABLE 2

VEGFR-2 AVG % Activity at Specific Concentration

| Compound | 3.0E−05 | 1.0E−05 | 3.0E−06 | 1.0E−06 | 3.0E−07 | 1.0E−07 | 3.0E−08 |
|---|---|---|---|---|---|---|---|
| sunitinib malate | 0 | −4 | −4 | 1 | 4 | 24 | 62 |
| mPEG$_3$-semaxanib | −6 | −3 | −3 | 0 | 16 | 47 | 78 |
| mPEG$_4$-semaxanib | −6 | −4 | −4 | 12 | 35 | 56 | 89 |
| mPEG$_5$-semaxanib | 0 | −4 | −1 | 17 | 34 | 70 | 93 |
| mPEG$_6$-semaxanib | −1 | −3 | 5 | 31 | 62 | 81 | 94 |
| mPEG$_7$-semaxanib | −6 | −3 | 0 | 19 | 46 | 80 | 90 |
| mPEG$_8$-semaxanib | −6 | −3 | 2 | 24 | 50 | 73 | 78 |
| mPEG$_9$-semaxanib | −1 | 1 | 8 | 20 | 46 | 61 | 71 |

| Compound | 1.0E−08 | 3.0E−09 | 1.0E−09 | 3.0E−10 | 1.0E−10 | IC$_{50}$ (nM) | Fold |
|---|---|---|---|---|---|---|---|
| sunitinib malate | 84 | 90 | 97 | 94 | 90 | 49.00 | |
| mPEG$_3$-semaxanib | 90 | 90 | 87 | 93 | 93 | 110.00 | 2.24 |
| mPEG$_4$-semaxanib | 88 | 96 | 92 | 97 | 86 | 180.00 | 3.67 |
| mPEG$_5$-semaxanib | 91 | 95 | 96 | 90 | 94 | 230.00 | 4.69 |
| mPEG$_6$-semaxanib | 99 | 96 | 95 | 85 | 93 | 520.00 | 10.61 |
| mPEG$_7$-semaxanib | 95 | 93 | 95 | 94 | 98 | 310.00 | 6.33 |
| mPEG$_8$-semaxanib | 85 | 82 | 86 | 84 | 86 | 430.00 | 8.78 |
| mPEG$_9$-semaxanib | 77 | 84 | 84 | 84 | 89 | 300.00 | 6.12 |

TABLE 3

RET AVG % Activity at Specific Concentration

| Compound | 3.0E−05 | 1.0E−05 | 3.0E−06 | 1.0E−06 | 3.0E−07 | 1.0E−07 | 3.0E−08 |
|---|---|---|---|---|---|---|---|
| sunitinib malate | −1 | −1 | −1 | 0 | 7 | 25 | 59 |
| mPEG3-semaxanib | −1 | −1 | 3 | 12 | 38 | 68 | 90 |
| mPEG4-semaxanib | −1 | 0 | 5 | 22 | 52 | 78 | 95 |
| mPEG5-semaxanib | −1 | 0 | 6 | 29 | 59 | 84 | 95 |
| mPEG6-semaxanib | 0 | 4 | 23 | 48 | 76 | 95 | 95 |

TABLE 3-continued

RET AVG % Activity at Specific Concentration

| | | | | | | | |
|---|---|---|---|---|---|---|---|
| mPEG7-semaxanib | 0 | 2 | 14 | 38 | 68 | 85 | 93 |
| mPEG8-semaxanib | 0 | 5 | 20 | 52 | 75 | 92 | 94 |
| mPEG9-semaxanib | 0 | 5 | 21 | 49 | 74 | 90 | 96 |

| Compound | 1.0E-08 | 3.0E-09 | 1.0E-09 | 3.0E-10 | 1.0E-10 | IC$_{50}$ (nM) | Fold |
|---|---|---|---|---|---|---|---|
| sunitinib malate | 83 | 92 | 97 | 98 | 98 | 43.00 | |
| mPEG3-semaxanib | 96 | 95 | 92 | 94 | 92 | 230.00 | 5.35 |
| mPEG4-semaxanib | 99 | 100 | 89 | 99 | 100 | 350.00 | 8.14 |
| mPEG5-semaxanib | 99 | 102 | 98 | 99 | 98 | 440.00 | 10.23 |
| mPEG6-semaxanib | 101 | 103 | 101 | 99 | 96 | 940.00 | 21.86 |
| mPEG7-semaxanib | 98 | 99 | 99 | 98 | 98 | 620.00 | 14.42 |
| mPEG8-semaxanib | 100 | 97 | 102 | 99 | 100 | 990.00 | 23.02 |
| mPEG9-semaxanib | 105 | 101 | 104 | 97 | 100 | 870.00 | 20.23 |

As tested by between 100 pM to 10 μM and as shown in the Table 1, the c-Kit activities of mPEG$_{3-9}$-semaxanib compounds are within about a five-fold of sunitinib. As shown in Table 2, the VEGR-2 activities of mPEG$_{3-9}$-semaxanib compounds are within about 10-fold of sunitinib. As shown in Table 3, the RET activities were lost up to 20-fold of sunitinib.

Example 3

Synthesis of Ethylene Glycol Linked PEG-Semaxanib Conjugates

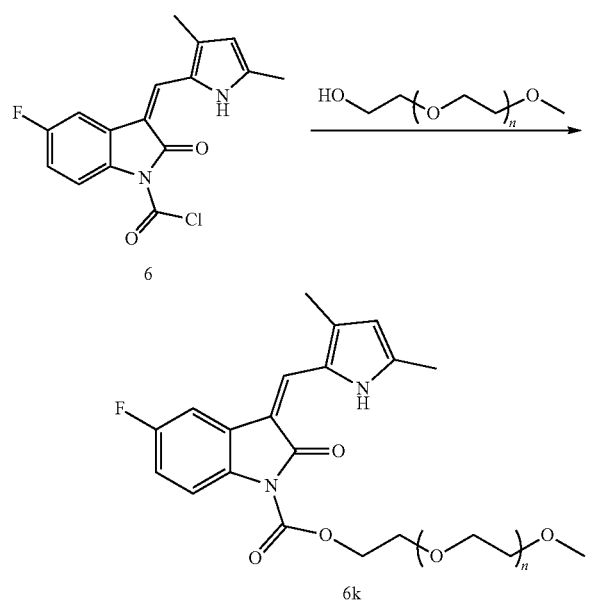

Synthesis of (Z)-3-((3,5-dimethyl-1H-pyrrol-2-yl)methylene)-5-fluoro-2-oxoindoline-1-carbonyl chloride (Compound 6)

In a 50 mL round-bottomed flask was suspended (Z)-3-((3,5-dimethyl-1H-pyrrol-2-yl)methylene)-5-fluoroindolin-2-one (semaxanib) (0.11 g, 0.47 mmol) in anhydrous THF (5 mL). The suspension was transferred to the triphosgene reaction in a second flask.

(Caution: To prevent release of toxic phosgene gas from either the reaction apparatus or rotary evaporator, the equipment setups were sparged through a sodium hydroxide scrub solution via an over pressure or exhaust port.) In a separate 50 mL round-bottomed flask was added triphosgene (1.6 g, 5.4 mmol) in anhydrous THF (40 mL) to give a colorless solution. Triethylamine (1.1 mL, 7.8 mmol) was added. After ten minutes, a semaxanib solution was transferred into this triphosgene solution. After approximately one hour, the reaction flask was placed on ice and cold 4M HCl solution (30 mL) was added to the flask. The crude product suspension was stirred for ten minutes, filtered and washed with cold 4M HCl solution (30 mL). The crude product was then placed under high vacuum for 18 hours in the presence of P$_2$O$_5$. Crude yield (Compound 6) was 0.12 g of a red solid. HPLC analysis was on a C18 silica column applying an acetonitrile gradient with 0.1% TFA; retention times observed were semaxanib 6.2 minutes and carbamoyl chloride product 7.4 minutes with ≥33% substitution at 280 nm. The carbamoyl chloride product was further characterized by reaction with excess n-butylamine (Z)—N-butyl-3-((3,5-dimethyl-1H-pyrrol-2-yl)methylene)-5-fluoro-2-oxoindoline-1-carboxamide and analyzed by HPLC. HPLC analysis was on a C18 silica column applying an acetonitrile gradient with 0.1% TFA; retention times observed were semaxanib 6.2 minutes and butylamine derivative 7.7 min with 81% substitution at 280 nm.

Synthesis of (Z)-(mPEG 20,000) 3-((3,5-dimethyl-1H-pyrrol-2-yl)methylene)-5-fluoro-2-oxoindoline-1-carboxylate (Compound 6k)

In a 50 mL flask was dissolved mPEG-OH 20K (0.5 g, 0.025 mmol) in anhydrous toluene. The solvent was evaporated under reduced pressure. The polymer was dissolved in anhydrous DCM (0.5 mL) and pyridine (0.02 mL, 0.23 mmol). To the polymer solution was added a suspension of crude (Z)-3-((3,5-dimethyl-1H-pyrrol-2-yl)methylene)-5-fluoro-2-oxoindoline-1-carbonyl chloride (Compound 6) (23 mg, 0.08 mmol) in anhydrous THF (2.5 mL). After one day, additional Compound 6 (28 mg, 0.1 mmol) was added. After ~3 days, the solvent was evaporated under reduced pressure to a thick oil. The crude product was dissolved in warm anhydrous IPA and slowly cooled to room temperature forming precipitate. The resulting slurry was filtered and washed with additional anhydrous IPA. Residual solvent was evaporated at reduced pressure. Yield was ~0.45 g of a solid powder. HPLC analysis was on a C18 silica column applying an acetonitrile gradient with 0.1% TFA; retention times observed were semaxanib 4.7 minutes and product 4.9 minutes with 96% purity at 280 nm and 59% purity by ELSD. $^1$H-NHR (d$_6$-DMSO): d (ppm) 2.3 (~3H, s, CH$_3$); 2.4

(~3H, s, CH$_3$); 3.2 (~3H, s, CH$_3$); 3.6 (~1800H, bs, PEG backbone); 4.5 (~2H, s, CH$_2$); 4.6 (<1H, m, OH); 6.1 (~1H, s, CH); 7.2 (~2H, m, Ar); 7.7 (~1H, s, CH); 7.8 (~1H, m, Ar); 7.9 (~1H, m, Ar); 12.6 (~1H, s, NH).

Example 4

Pharmacokinetic Study

A pharmacokinetic study of sunitinib and the mPEG$_{3-9}$-semaxanib compounds prepared in accordance with Example 1 were evaluated in a standard pharmacokinetic study. Briefly, male Sprague Dawley rats with jugular vein and carotid artery catheters for intravenous dosing and carotid artery catheters only for oral dosing were obtained from Charles River Labs. (Wilmington Mass.). The rats were fasted overnight prior to dosing. Food was returned after the four-hour timepoint. Each test article was assigned a group of three animals and plasma concentration values represent the mean of the values obtained.

For intravenous administration, a one mL syringe was used and the animals were dosed 2 mg/kg intravenously using the jugular vein catheter. The dead volume of the catheter was flushed with saline to ensure the animals received the entire dose. Plasma samples were collected at 0.03, 0.25, 0.5, 1, 2, 4, 6, 24 and 48 hours post dose.

For oral administration, animals were dosed orally by gavage using a one mL syringe and a gavage needle (18 G×2 inches, Popper & Sons Inc., New Hyde Park, N.Y.). Plasma samples were collected at 0.08, 0.25, 0.5, 1, 2, 4, 8, 24 and 48 hours post dose.

All test articles were administered with 0.9% saline and all doses were kept on ice with syringes filled immediately prior to dosing. At the 20 mg/mL dosage, the mPEG$_{3-5}$-semaxanib compounds were not soluble in saline; consequently, the dose for these compounds was diluted to 10 mg/mL and the dose volume doubled.

Figure 2:
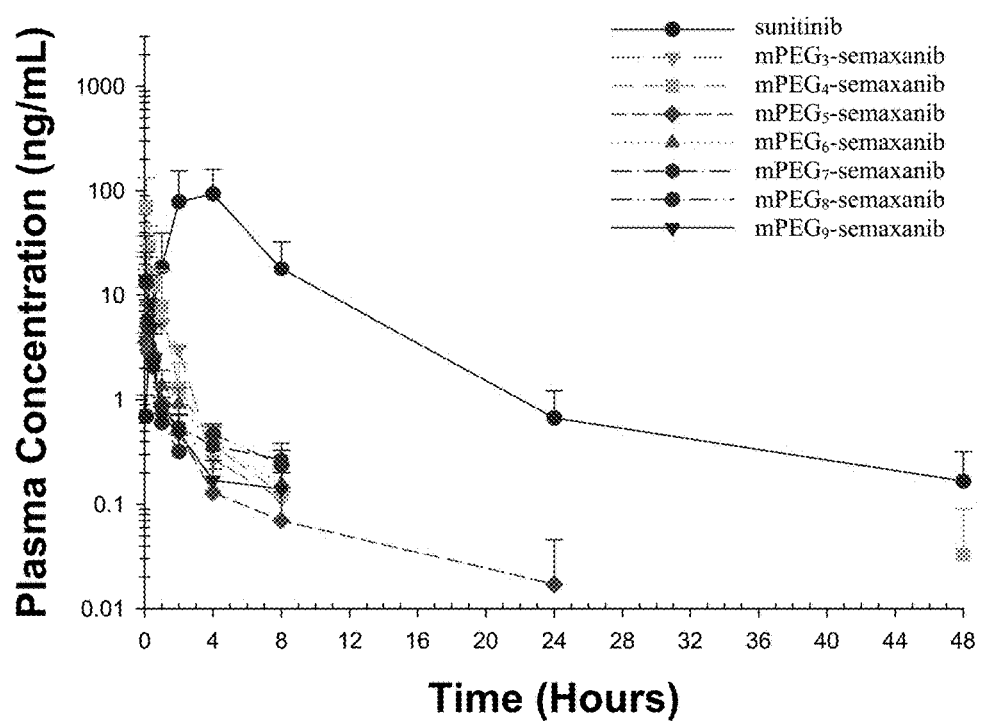
FIG. 2 is a plot of the mean plasma concentration values of sunitinib and mPEG$_{3-9}$-semaxanib compounds following 2 mg/kg oral dosing in rats, as further discussed in Example 4.
Figure 3:
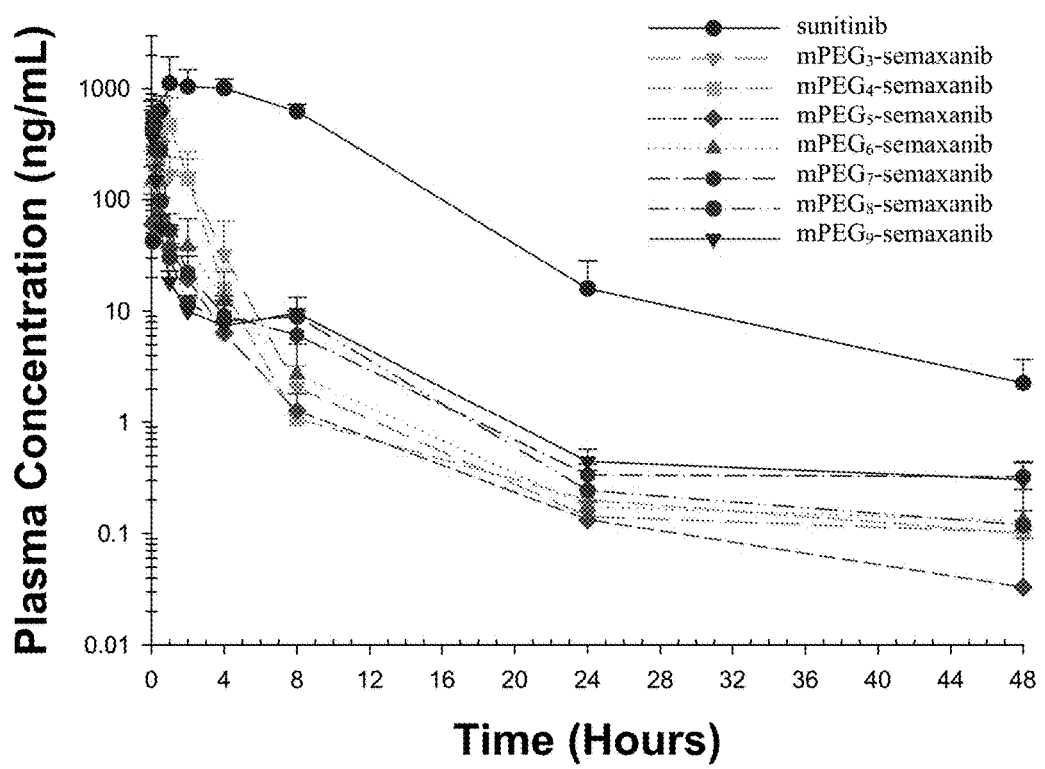
FIG. 3 is a plot of the mean plasma concentration values of sunitinib and mPEG$_{3-9}$-semaxanib compounds following 20 mg/kg oral dosing in rats, as further discussed in Example 4.

Provided as plots, the mean plasma concentration values for tested articles after 2 mg/kg intravenous dosing (FIG. 1), after 2 mg/kg oral dosing (FIG. 2), and 20 mg/kg oral dosing (FIG. 3) in rats were determined.

What is claimed is:

1. A method of treating a glioma comprising:
    administering a therapeutically effective amount of a compound to a subject in need thereof, the compound having a formula:

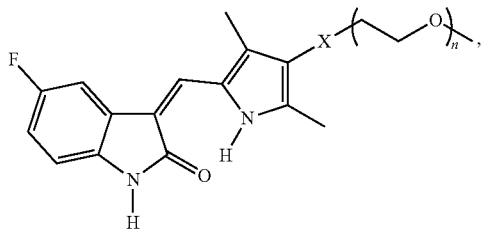

or pharmaceutically acceptable salts thereof wherein:
    X is a spacer moiety selected from a single bond, an ether, an amide, a urethane, an amine, a thioether, a carbamate, an ester, a carbonate, and a urea linkage; and
    n is an integer from 3 to 10.

2. The method of claim 1, wherein said administering comprises orally administering the compound.

3. The method of claim 2, wherein said orally administering comprises administering the compound in the form of a tablet, caplet, capsule, gel capsule, troche, dispersion, suspension, solution, elixir, or syrup.

4. The method of claim 1, wherein said administering comprises parenterally administering.

5. The method of claim 4, wherein said parenterally administering is selected from subcutaneous, intravenous, intra-arterial, intraperitoneal, intramuscular, and infusion.

6. The method of claim 1, wherein said administering comprises administering about 0.001-1000 mg/day of the compound.

7. The method of claim 1, wherein said administering comprises administering the compound five times a day, four times a day, three times a day, twice daily, once daily, three times weekly, twice weekly, once weekly, twice monthly, or once monthly.

8. The method of claim 1, wherein the compound has the formula:

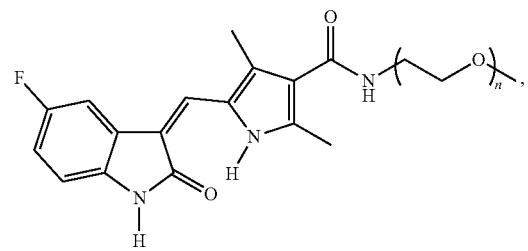

or a pharmaceutically acceptable salt thereof.

9. The method of claim 1, wherein the glioma is mediated by abnormal vascular endothelial growth factor (VEGF) receptor tyrosine kinase activity.

10. The method of claim 1, wherein the glioma is a glioblastoma.

11. The method of claim 1, wherein said administering comprises administering about 0.01-750 mg/day of the compound.

12. The method of claim 1, wherein said administering comprises administering about 0.10-500 mg/day of the compound.

* * * * *